Nov. 12, 1946. R. L. BYRUM Plant Pat. 715
ROSE PLANT
Filed Oct. 24, 1945
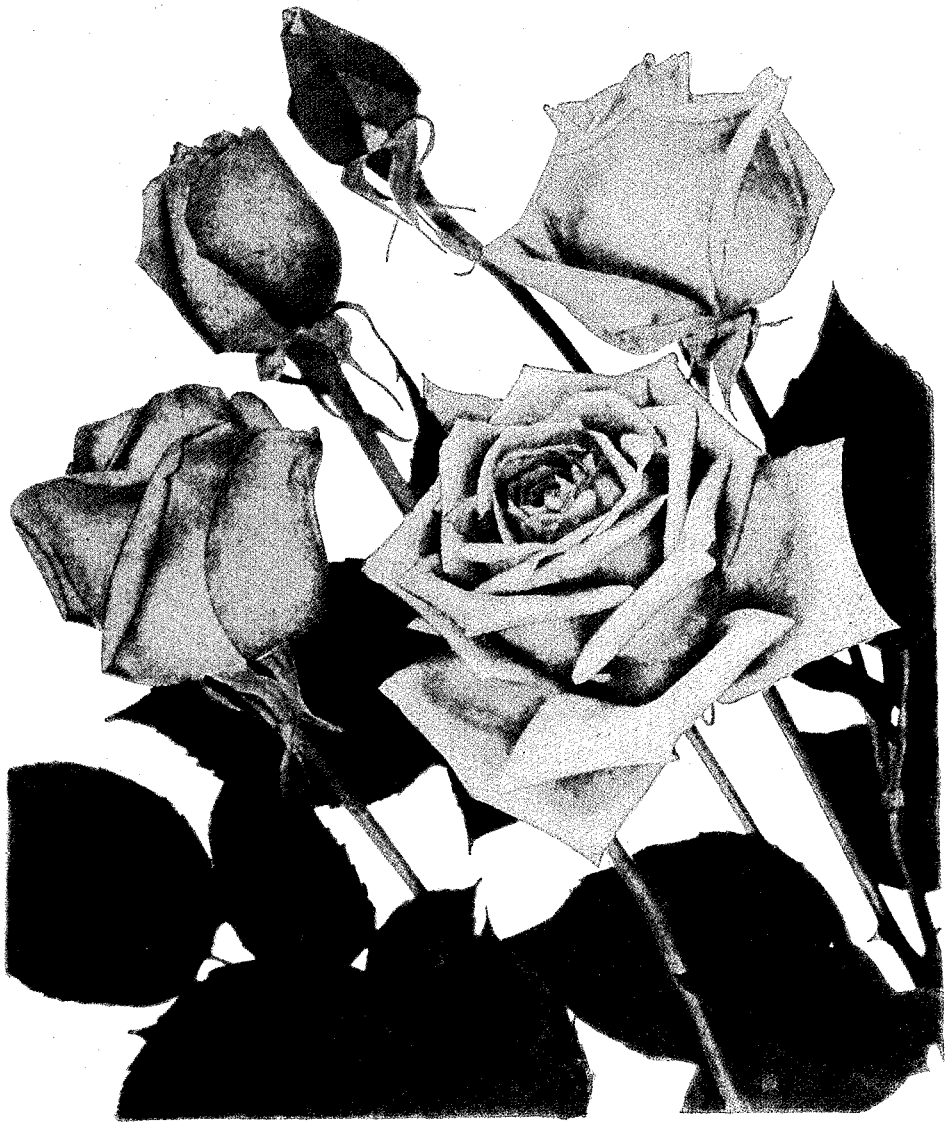
Inventor
Roy L. Byrum
By Robbins & Robbins
Attorneys Patented Nov. 12, 1946

Plant Pat. 715

UNITED STATES PATENT OFFICE

715

ROSE PLANT

Roy L. Byrum, Richmond, Ind., assignor to Joseph H. Hill Company, Richmond, Ind., a corporation of Indiana Application October 24, 1945, Serial No. 624,230

1 Claim. (Cl. 47—61)

The present invention relates to a new and distinct variety of rose plant, especially useful for greenhouse forcing for cut-flower purposes.

This new variety is the result of a crossing of two well-known varieties, "Chieftain" (Pl. Patent #150) and "Lucile Hill" (Pl. Patent #305) and is markedly distinguished from either of its parents as will hereinafter more fully and specifically appear.

The primary features of distinction are the large size of the blooms, larger than any greenhouse forcing red variety of which I am aware; more vigorous habit of growth than any greenhouse red variety in general use today; and the distinctive red color (particularly notable for the brilliant reaction of petal color and texture under Mazda lights), together with size and freedom of blooming on long, strong stems.

Asexual reproduction of this new variety shows the foregoing characteristics come true to form and are established.

In the drawings are shown specimens of the rose, showing the development of the flower from bud to full blown stages.

The following is a detailed description of the new variety, color terminology being in accord with Ridgway's Color Standard, except where otherwise indicated to have ordinary dictionary significance:

Type: Tall; bush; greenhouse; seedling; for cut flowers.

Class: Hybrid, tea.

Breeding: Seedling.

*Seed parent.*—"Chieftain."

*Pollen parent.*—"Lucile Hill."

Propagation: Holds its distinguishing characteristics through succeeding propagations by cutting, grafting, and budding. Layering not yet tried.

Locality where grown: Richmond, Indiana.

Flowers borne: Singly to stem on strong, long stems.

Quantity of bloom: Abundant, in greenhouse.

Continuity: Continuous.

Fragrance: Strong; tea.

Bud:

*Peduncle.*—Long; heavy; stiff; light green; almost smooth; few yellow hairs.

*Before calyx breaks.*—*Size*—large. *Form*—short; pointed; ovoid, with a conspicuous neck; with foliaceous appendages on the surface of the bud; with slender, foliaceous parts extending beyond the tip of the bud equal to one-half or more of its length.

*As calyx breaks.*—*Color*—Carmine, Plate 1, edged with Maroon, Plate 1.

*As first petal opens.*—*Size*—large. *Form*—long; flat; pointed. *Color*—outside: Carmine, Plate 1, washed with Victoria Lake, Plate 1; inside: Carmine, Plate 1, overlaid with velvety Ox-blood Red, Plate 1.

*Opening.*—Opens up well.

Bloom:

*Petalage.*—Very double; 55 to 60 petals; arranged irregularly.

*Form.*—Very full; globular at first, becoming open; petals remaining at first very tightly rolled outward; becoming later, at maturity, loosely rolled outward.

Petals: Thick; with inside velvety and outside shiny.

*Shape.*—Outside—obovate with apex flat. Intermediate—obovate with apex flat. Inside—obovate, some scalloped, some with one notch.

This description of a newly opened flower was made from a rose grown in a greenhouse in the month of January, at Richmond, Indiana:

*Color.*—*Outside petal*—outside surface: Rose Red, Plate 12, overlaid with Pomegranate Purple, Plate 12; inside surface: Rose Red, Plate 12, overlaid with Velvety Rose Red. *Intermediate petal*—outside surface: Rose Red, Plate 12, overlaid with Pomegranate Purple, Plate 12; inside surface: Rose Red, Plate 12, overlaid with Velvety Rose Red. *Inner petal*—outside surface: Rose Red, Plate 12, overlaid with Pomegranate Purple, Plate 12; inside surface: Rose Red, Plate 12, overlaid with Velvety Rose Red.

This description was made from a rose that was open for three days in a greenhouse in the month of January, at Richmond, Indiana:

*Color.*—*Outside petal*—outside surface: Rose Red, Plate 12, washed with Rose Color, Plate 12; inside surface: Tyrian Rose, Plate 12. Inside petal—outside surface: Rose Red, Plate 12; inside surface: Tyrian Rose, Plate 12.

*General color effect.*—Newly opened flower—Rose Red, Plate 12. Three days open—Tyrian Rose, Plate 12.

*Behavior.*—Persistent; not easily affected by weather in greenhouse.

*Flower longevity.*—Cut rose grown in greenhouse kept at living room temperatures—4 to 5 days in December.

*Reproductive organs*

Stamens: Medium number, arranged regularly about pistils.
Filaments: Short; reddish, most with anthers.
Anthers: Small; brown, all open at once.
Pollen: Moderate; gold.
Pistils: Many.
Styles: Uneven; short; thin; bunched.
Stigma: White.
Ovaries: Some protruding from calyx.
Hips: Ovoid, with inconspicuous neck; green; turning to yellow when ripe; very smooth. *Color*—Pois Green, Plate 41.
Sepals: Permanent; short; spear-shaped; curled. *Color*—inside: Light Cress Green, Plate 31; outside: Cress Green, Plate 31.
Seeds: Few; medium size.

*Plant*

Foliage:
*Leaves.*—Compound of 5, very abundant; very large; leathery.
*Leaflets.*—Ovoid, with apex acute; base obtuse; margin simply serrate.
*Color.*—*Mature*—upper surface: Dark Green; under surface: moderately Light Green. *Young*—upper surface: Bronze-Red; under surface: Bronze-Red.
*Rachis.*—Heavy; grooved; smooth.
*Stipules.*—Long; medium width; with medium points turning out at an angle of more than 45°.
*Disease.*—Resistant to mildew and blackspot.
Growth:
*Habit.*—Bush; upright; much branched.
*Growth.*—Free; vigorous.
*Canes.*—Heavy.
*Main stems.*—Dull bronze. *Thorns*—several; short; hooked downward with short narrow base. *Prickles*—none. *Hairs*—none.
*Branches.*—Bright green. *Thorns*—several; short; hooked downward, with short narrow base. *Prickles and hairs*—none.
*New shoots.*—Bright bronze red. *Thorns*—several; short; straight with short narrow base. *Prickles and hairs.*—none.

Since the present variety of rose is somewhat similar to the well-known variety "Better Times," Plant Patent #23, it is desirable to note the distinctions between these two varieties as follows:

(1) In the case of the present variety, the number of petals is 50 to 60, while in the case of "Better Times," the number is 30 to 35.

(2) The size of the bud before calyx breaks is large for the present variety while in the case of "Better Times" it is medium large.

(3) The size of the bud as first petal opens is large as to the present variety while in the case of "Better Times" it is medium large.

(4) The size of the bloom is very large as to the present variety and only large as to "Better Times."

(5) There is a very noticeable difference in the new soft growth of the two varieties. In the present instance it is light green, while in the case of "Better Times" it is bronze red.

(6) The general appearance of a house of this new variety while in soft growth is green, while the general appearance of a house of "Better Times" in soft growth is red. The present variety has a heavier cane than "Better Times," but this could vary during certain times of the year and under certain cultivation.

(7) The foliage of this new variety is not as leathery as "Better Times," but is much more wrinkled on the young growth.

| | Comparison of color | |
|---|---|---|
| | Present variety | "Better Times" |
| | *Seedling* | *Sport* |
| As calyx breaks | Carmine, Pl. 1 | Amaranth Purple, Pl. 12. |
| As first petal opens | do | Tyrian Rose, Pl. 12. |
| Outside petal: | | |
| Outside surface. | Rose Red, Pl. 2 | Rose Color, Pl. 12. |
| Inside surface. | do | Tyrian Rose, Pl. 12. |
| Intermediate and inner petals. | Same as outside petals. | Same as outside petals. |
| Open three days: | | |
| Outside and inside petals— | | |
| Outside surface. | Rose Red, Pl. 12 | Tyrian Pink. |
| Inside surface. | Tyrian Rose, Pl. 12 | Do. |
| General color effect: | | |
| Newly opened flower. | Rose Red, Pl. 12 | Tyrian Rose, Pl. 12. |
| Three days open | Tyrian Rose, Pl. 12 | Rose Color, Pl. 12. |

I claim:

A new and distinct variety of Hybrid Tea Rose plant, characterized as to novelty by the vigorous habit of growth of the plant, large size of the blooms; freedom of blooming on long, strong stems, and the unusual red color of the blooms, with brilliant reaction of petal color and texture under certain lighting conditions, in the class of greenhouse forcing varieties, substantially as shown and described.

ROY L. BYRUM.